United States Patent [19]

Tribble et al.

[11] 4,122,166

[45] Oct. 24, 1978

[54] INJECTABLE CONTRACEPTIVE AND METHOD

[75] Inventors: Ronald L. Tribble, Savannah; Charles M. Stagg, St. Joseph, both of Mo.

[73] Assignee: Philips Roxane, Inc., St. Joseph, Mo.

[21] Appl. No.: 880,508

[22] Filed: Feb. 23, 1978

Related U.S. Application Data

[63] Continuation of Ser. No. 715,164, Aug. 17, 1976, abandoned.

[51] Int. Cl.$^2$ .................. A61K 37/24; A61K 39/00
[52] U.S. Cl. ........................................ 424/88; 424/85; 424/100; 424/105; 424/177; 424/238
[58] Field of Search .................. 424/85, 88, 100, 105, 424/177, 238–243

[56] References Cited

PUBLICATIONS

C.A.84, #159864r, #159865s (1976).
C.A.83, #191210q, #188650c, #129524s (1975).
C.A.80, #23006x, #106544x (1974).
C.A.79, #64420a (1973).
C.A.77, #56941q (1972).
C.A.84, #40423f, #40425h (1976).
C.A.82, #122178c, #122179d, #151517t, #151518u, #151519v (1975).
C.A.81, #48386e (1974).
C.A.79, #51604p, #64068s, #16679v, #112892e (1973).
C.A.77, #101991u.
C.A.77, #31179j, #147777g, #147778h (1972).
C.A.76, #97742y, #138870j (1972).

Primary Examiner—Shep K. Rose

[57] ABSTRACT

An injectable contraceptive antiserum, a process of preparing said antiserum and the method of preventing conception in mammals by the use of said antiserum, is disclosed. An antigen which causes the production of antibodies directed against a hormone essential to the reproductive cycle of mammal is prepared by coupling such a hormone with a carrier to form a hormone-carrier conjugate. A mammal is injected with said conjugate, and the produced antiserum is recovered from blood obtained from said mammal. Conception in mammals is prevented by injection of such recovered antiserum during the proper period of the reproductive cycle of said mammal.

Specifically described is the antiserum recovered from the blood of a mammal which has been injected with an antigen prepared by coupling a hormone, such as, estradiol-17 beta with a protein and its use to temporarily sterilize a female of the canine species.

8 Claims, No Drawings

INJECTABLE CONTRACEPTIVE AND METHOD

This is a continuation, of applicaton Ser. No. 715,164, filed Aug. 17, 1976, now abandoned.

SUMMARY OF INVENTION

This invention relates to a contraceptive antiserum, to a process of its preparation and to a method for the prevention of conception in female mammals by the properly timed use of such antiserum.

Particularly, the invention relates to a contraceptive antiserum to an estrogen, which estrogen is essential to the reproductive cycle of a female mammal, and which antiserum has been produced by the immunological system of a member of the same species.

Still more particularly, the invention comprises a contraceptive antiserum against the estrogen, estradiol-17 beta ($E_2$), which antiserum is prepared by injecting the $E_2$ — protein conjugate into a mammal, either male or female, recovering from the blood of such mammal the antiserum produced by its immunological system, and using such recovered antiserum as a contraceptive for, or for the temporary sterilization of, a female mammal.

GENERAL DESCRIPTION OF INVENTION

There exists today a considerable interest on the part of those concerned with animal husbandry, and others, in the prevention of conception, at least for some period of time, in most mammals, whether they be humans, dogs, cats, cattle, sheep, horses, pigs, or the like. Consequently, there have been many methods derived to accomplish this end, all of which are undesirable in one respect or another. For example, clinical surgery (castration, ovari-hysterectomy) has its obvious faults. Mechanical contraception is likewise undesirable for various reasons and chemotherapeutic agents are not only unreliable, but also many times induce undesirable side effects in many mammals.

It has long been known that female mammals produce estrogen which is necessary for the manifestation of estrus, ovulation and implantation. If the mammalian body were to produce its own antibodies against such a requisite estrogen, fertility would not exist.

The natural occuring estrogen molecule in the mammalian body is non-antigenic and therefore will not stimulate the production of antibodies of said estrogen in the body of said mammals.

The present invention involves producing an antigen which, when injected into a host mammal, will produce an antiserum against a requisite estrogen. This is accomplished by first making an antigen by coupling an essential estrogen with a carrier and injecting such antigen into the mammal desired for antiserum production. The mammal is then bled to recover the antiserum produced by said mammal and said antiserum is harvested. Any female mammal of the same species as the host mammal may be injected with the antiserum at the proper time prior to ovulation and the injected antiserum will cause temporary sterilization of, or prevent conception of, said mammal.

Of particular interest, and contemplated in one preferred embodiment of this invention, is a contraceptive antiserum against the estrogen, estradiol-17 beta ($E_2$), which antiserum has been found useful to control canine reproduction.

It has been found that if the contraceptive antiserum against the estrogen, estradiol-17 beta, is given to a female dog during the optimal time, (late anestrus-early proestrus into midproestrus), one can expect a complete bypass of the upcoming estrus period. Once treated, the bitch will return to estrus at the next expected time, approximately 5–8 months later with no impairment of fertility. If the antiserum is administered anytime prior to the late anestrus — early proestrus period, one can only be sure of a short term (approximately 3 week) period of contraception. This can be advantageous when the pet owner wants assurance that his bitch will not be in heat for a specified time such as hunting, racing, showing, etc. If the antiserum is given during late proestrus the percent efficacy is drastically reduced. The antiserum is without effect if injected during the estrus period.

The preparation of the novel contraceptive antiserum of this invention may be generally described as follows.

The antigen of the present invention comprises a steroid-carrier conjugate which has been found to be effective in producing specific antibodies against the steroid. For example, an estrogen such as estradiol-17 beta, are rendered antigenic by covalent attachment to a carrier containing amino groups. The carrier selected for use in the production of the antigen may be, for example, any protein or polypeptide, which, when combined with the said estrogen molecule, will render the said steriod-carrier conjugate antigenic.

In one specific embodiment of the inventive concept, the conjugation of the estradiol-17 beta to the amino groups of the carrier used, as for example Keyhole Limpet Hemocyanin, is effected by preparing the hemisuccinate of the estrogen molecule, which hemisuccinate is then coupled to the carrier via the carbodiimide reaction.

As is well known in the art, other estrogens may be rendered antigenic by coupling to other carriers by known chemical reactions. For example, estrogens such as estradiol-17 alpha, estrone, estriol, equilin, equilenin, and the like may be coupled to a carrier which, in itself, may be antigenic, or may be modified to become antigenic. Examples of such carriers in addition to Keyhole Limpet Hemocyanin (KLH) are Bovine Serum Albumin (BSA), Human Serum Albumin (HSA), and the like.

A derivative of the desired estrogen is prepared, for example, by esterification of the hydroxyl groups of the estrogen with succinic anhydride, formation of oxime derivatives of the ketone groups of the estrogen using (o-carboxymethyl) hydroxylamine, and the like, and the derivative is then coupled to the carrier by use, for example, of Schotten-Baumann method, the mixed anhydride method, the carbodiimide condensation, and the like. These techniques are well known to the art. See for example Thorneycroft, I. H. (1970) Preparation and Purification of Antibodies to Steroids. Immunologic Methods in Steroid Determination, Appleton-Century-Crofts, 63–86; Lindner, et al. 1972. Specificity of Antibodies to Ovarian Hormones in Relation to the Site of Attachment of the Steroid Hapten to the Peptide Carrier. Steroids 19:357; Mahajan, D. K., et al, 1972. Plasma 11 — Deoxycortisol Radioimmunoassay for Metyrapone Tests. Steroids 20:609; Yellin, T. O. 1972. Estradiol-17-Beta-Hemisuccinate: An improved Procedure. J. Lipid Res. 13:554; Lieberman, et al. 1959 Steroid-Protein Conjugates: Their Chemicals Immunochemical, and Endocrinological Properties, Rec. Prog. Hor. Res. 15:165.

The prior art has also described the use of various estrogen antibodies in the investigation of mechanism of the reproductive cycles of mice, (Ferin, M. et al, 1968. Inactivation of the Biological Effects of Exogenous and Endogenous Estrogens by Antibodies to 17B-Estradiol. Endocrinology 83:565.), rats, (Ferin, M. A. et al, 1969. Effect of Antibodies to 17B-Estradiol and Progesterone on the Estrous Cycle of the Rat. Endocrinology 85:1070) and sheep; (Scaramuzzi, R. J. 1975. Inhibition of Oestrous Behavior in Ewes by Passive Immunization Against Oestradiol-17B, J. Reprod. Fert. 42:;45.)

The antiserum of the present invention may be produced for the purpose of temporary sterilization of mammals by injecting $E_2$-carrier conjugate into a male or female donor mammal of the same species as the recipient and by recovering such antiserum.

The donor species is injected with the desired amount of antigen. The antigen is injected parenterally, preferably both intradermally and intramuscularly. After an initial injection, the donor is boostered periodically in order to maintain a satisfactory antibody level.

When it has been determined that satisfactory antibody levels exist, blood is collected from such donor and the serum or plasma containing the antibodies is separated. This blood serum or plasma, containing antibodies to the desired estrogen, the antiserum of this invention, may be used directly as a contraceptive antiserum, or it may be stabilized and processed in accordance with known techniques into individual unit dosages.

The invention will be more clearly explained by reference to the following specific description and experimental data.

PRODUCTION OF ANTIGEN

The antigen of one preferred embodiment of this invention consists of a steroid-protein conjugate found to be effective in producing specific antibodies against the steroid, Estradiol-17 Beta ($E_2$) residue. Estradiol-17 Beta is rendered antigenic by covalent attachment to the protein Keyhole Limpet Hemocyanin (KLH). Coupling to epsilon-amino groups of the lysine residues of KLH is affected via the 17-beta hemisuccinate by the use of the carbodiimide reagent. The complete conjugation procedure employed is a modification of procedures employed by previous researchers.

1. Preparation of estrogen derivative

Five grams of $E_2$ (Calbiochem, San Diego, Cal.) and 25 micro-Curies (uCi) of $^3$H-6, 7-estradiol-17 beta ($^3$H-$E_2$) (New England Nuclear, Boston, Mass.) are added to a 500 ml round-bottom flask. Next, 250 ml benzene containing 1% pyridine and 15 gm succinic anhydride are added to the same flask and the contents refluxed for 40 hours. The solvent is then evaporated and the remaining residue is dissolved in 625 ml methanol. To the solution is added 100 ml of a 15% solution of sodium bicarbonate and the contents are stirred overnight. The contents are filtered and an equal volume of water is added. The solution is then extracted three times with 200 ml portions of diethyl ether. The remaining aqueous phase is adjusted to pH7 with 6 N HCL and poured into a mixture of 0.2 N HCL and crushed ice (1:1). The precipitate estradiol-17 beta hemisuccinate ($E_2$-HS) is collected by filtration, washed with water and dried in vacuo at 37° C.

The general chemical scheme leading to the formation of the estradiol-hemisuccinate is as follows:

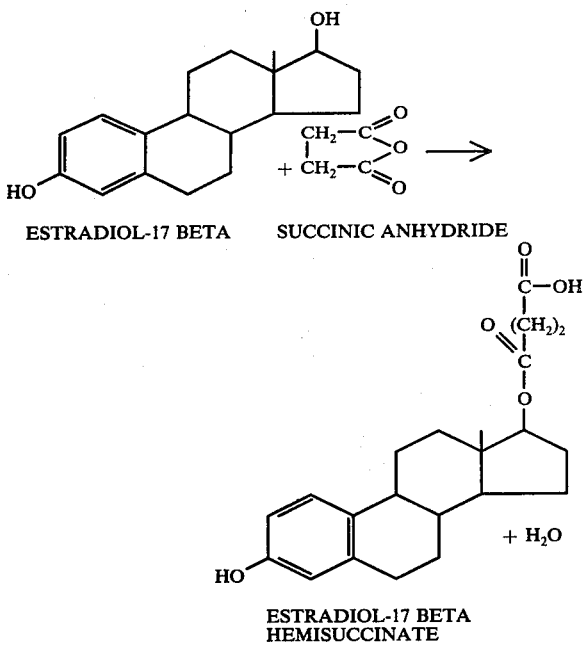

In order to subsequently determine the number of moles of $E_2$ which are attached to a mole of protein, the disintergrations per minute per mg $E_2$-HS (DPM/mg $E_2$-HS) must be determined. To accomplish this, 45 to 55 mg of accurately weighed $E_2$-HS is placed into a liquid scintillation counting vial. To the vial is also added 0.1 ml water and 1 ml of Soluene-350 (solubilizer, Packard Instrument Co., Downers Grove, Ill.) and the contents are allowed to stand until the residue is completely digested. After this digestion, 10 ml of Dimilume (Scintillation media, Packard Instrument Co.) is added and the contents of the vial are counted for radioactivity. The DPM/mg $E_2$-HS is then determined based upon counts per minute (CPM), scintillation counter efficiency and weight of $E_2$-HS. The DPM/mg $E_2$-HS is calculated in the following manner:

Example

CPM = 90,000
Weight of $E_2$-HS = 50 mg
efficiency = 40%

$$DPM = \frac{CPM}{\text{efficiency}} = \frac{90,000}{0.4} \quad 225,000/50 \text{ mg } E_2-HS$$

$$DPM/\text{mg } E_2-HS = \frac{225,000}{50} = 4500$$

2. Conjugation of Estrogen derivative to carrier

Five grams of KLH (Calbiochem) is dissolved in 250 ml of water and the pH is adjusted to 7.5. With constant stirring, 2.5 gm of water-soluble carbodiimide (1-ethyl-3 (3-di-methyl amino propyl) — carbodiimide) is added while maintaining the above pH with dilute HCL. There is added dropwise 50 ml of dimethyl formamide containing 2.5 gm $E_2$-HS with constant stirring while maintaining the pH at 7.5 with 1 N NaOH. The reaction mixture is equilibrated at room temperature for 2 hours, after which an additional 500 mg of the carbodiimide is added. After an additional 20 hour equilibration, the mixture is dialyzed against water for 48 hours. The steroid-protein conjugate is precipitated by the addition of 90 ml of acetone for each 10 ml of solution remaining in the dialysis bag. The residue is collected by filtration, washed with acetone and dried in vacuo at 37° C.

The general chemical scheme leading to the formation of $E_2$-KLH from $E_2$-HS is as follows:

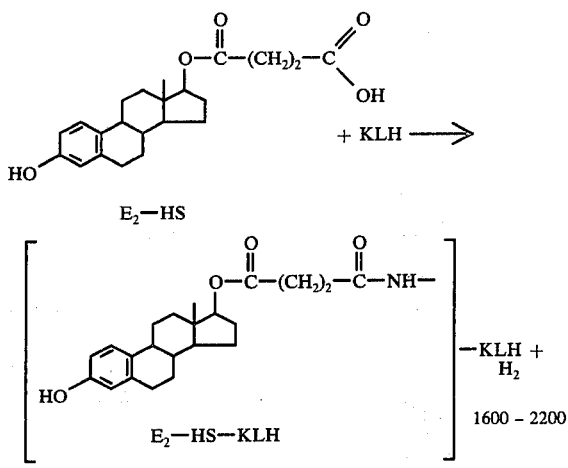

3. Testing of Antigen

Ten to 15 mg of accurately weighed steroid-protein conjugate ($E_2$-KLH) is placed into a liquid scintillation counting vial. To the vial is added 0.1 ml water and 1 ml of Soluene — 350 and the contents are allowed to stand until the residue is completely digested. After this digestion, 10 ml of Dimulume is added and the contents of the vial are counted for radioactivity. The number of moles of $E_2$ which is attached to one mole of KLH is calculated in the following manner:

Example

1. Molecular weight (M.W.) of KLH = $6 \times 10^6$ gm/mole
2. DPM/mg $E_2$-HS as determined under 1. above — 4500 DPM/mg $E_2$-HS
3. M.W. of $E_2$-HS = 372 gm/mole
4. 6000 DPM/10mg of $E_2$-KLH Calculations:

$$\frac{6000 \, DPM/10 \, mg}{4500 \, DPM/mg \, E_2-HS} \times 1.33 \, mg \, (0.00133 \, gm) \, E_2-HS$$

$$\frac{0.00133 \, gm \, E_2-HS}{372 \, gm/Mole} = 3.575 \times 10^{-6} \, \text{Mole of } E_2-HS$$

$$\frac{0.010 \, gm \, KLH}{6 \times 10^6 \, gm/Mole} = 1.67 \times 10^{-9} \, \text{Mole of } KLH$$

$$\frac{\text{Moles } E_2HS}{\text{Moles } KLH} = \frac{3.575 \times 10^{-6}}{1.67 \times 10^{-9}} = 2140$$

It has been found, and forms an important part of the inventive concept, that the $E_2$-KLH antigen is most effective in producing specific antibodies against the steroid moiety when the number of $E_2$-HS molecules incorporated per molecule of KLH is between 1600 and 2200.

PRODUCTION OF ANTISERUM

As was stated above, the antiserum of this invention is prepared by injecting the $E_2$ protein conjugate, prepared as described above, into a donor mammal, either male or female, and recovering from the blood of such mammal the antiserum produced by its immunological system. In a preferred embodiment of this invention, the donor mammal is of the same species as the subsequent recipient of the antiserum. Especially preferred are females of the canine species. Such antiserum preparation is described in detail below.

Each donor dog receives an initial innoculation of 1 mg $E_2$-KLH emulsified in 2 ml of adjuvant with a concentration of 0.5 mg/ml. The adjuvant consists of an emulsion containing by volume:
- 25% Physiological Sterile Saline
- 25% Complete Freund's Adjuvant
- 50% Peanut Oil Emulsion containing 2% Aluminum Monosterate One ml is injected into multi-intradermal sites. The other 1 ml is injected into 2 intramuscular (I.M.) sites. Twenty-eight to 31 days later each donor dog receives 10 mg $E_2$-KLH emulsified in 2 ml of the same adjuvant. One ml is injected into each of 2 I.M. sites. Thereafter, each dog is boostered every 2 weeks with 1 mg $E_2$-KLH emulsified in 2 ml of the adjuvant. One ml is injected into each of the 2 I.M. sites.

Seven to 9 days following each booster injection the donor dogs are bled for antiserum recovery. Each donor dog is weighed prior to bleeding. Approximately 25% of the blood volume is removed via cardiac or jugular at each bleeding. Each donor dog is bled into a plastic container containing an anticoagulant (50 ml of a 4% sodium citrate solution). Blood plasma is retrieved from each bag by centrifugation and pooled in glass containers.

To the pooled plasma there is added 3.07 gm calcium cholride per liter of plasma and immediately the plasma containers are placed on a mechanical shaker for defibrination. Clear antiserum is obtained by filtration through cheesecloth. A 1% solution of buffered Thimerosal preservative is added to the antiserum to obtain a final concentration of 1:10,000. The antiserum is then sterile filtered through a Millipore filter. The sterile antiserum is assayed for titer and subsequently diluted or concentrated as the assay indicated. This standardized antiserum is added to individual dosage bottles and subsequently lyophilized.

The antiserum is titered for antibodies against $E_2$ by the capacity of the antiserum to bind the radioactive form of $E_2$, $^3$H-6,7-estradiol-17 beta ($^3$H-$E_2$). Serial dilutions of each lot of antiserum are carried out to obtain an end point binding of approximately 50% of the $^3$H-$E_2$ added. The dilution of antiserum that gives approximately 50% binding is used to calculate the proper dosage. Using the various antisera dilutions, a sigmoid curve is obtained and 50% binding fits into the linear most portion of the curve. A charcoal suspension is used to separate antibody bound $^3$H-$E_2$ from free $^3$H-$E_2$. If one adds 10,000 cpm $^3$H-$E_2$ and after charcoal separation finds 5000 cpm of $^3$H-$E_2$ bound to the antibody, one therefore achieves a 50% binding at a particular antiserum dilution.

In order to calculate the amount of $^3$H-$E_2$ bound in each tube per dilution, the mass of the original $^3$H-$E_2$ added must be determined as shown in the following calculation:

Example

1. M. W. of $^3$H-$E_2$ = 272.4 gm
2. Specific Activity of $^3$H-$E_2$ = 49.3 Ci/m Mole
3. $2.22 \times 10^6$ DPM per uCi 4. cpm $^3$H-E$_2$ added per culture tube = 10,414
5. 1 gm = 1 × 10$^{12}$ picograms (pg)
6. Efficiency of counting = 46.6%

Therefore:
1. 49.3 Ci = 49.3 × 10$^6$ uCi
2. mMole of $^3$H-E$_2$ = 0.2724 gm (49.3 × 10$^6$ uCi) (2.22 × 10$^6$ DPM/uCi) = 109.446 × 10$^{12}$ DPM/0.2724 gm.

$$\frac{109.446 \times 10^{12} DPM}{0.2724 \text{ gm}} = 401.78 \times 10^{12} DPM/gm$$

$$\frac{401.78 \times 10^{12} DPM/gm}{1 \times 10^{12} pg} = 401.78 \ DPM/pg$$

$$DPM = \frac{CPM}{\text{efficiency}} = \frac{10,414}{0.466} = 22,348 \ DPM$$

$$\text{Mass (pg) added} = \frac{22,348 \ DPM}{401.78 \ DPM/pg} = 55.6 \ pg$$

Once the mass of $^3$H-E$_2$ has been determined, the binding capacity of the antiserum can be calculated as shown in TABLE I below.

TABLE I

Binding Capacity of the Antiserum

| Serum Dilution (ml) | CPM | %$^3$H-E Bound$^2$ (CPM/ 10,414) | pg$^3$H-E$_2$ Bound$^2$ (% bound × 55.6) | Factor | pg $^3$ H-E$_2$ Bound per ml serum |
|---|---|---|---|---|---|
| 1/100* | 8346* | 77.9* | 44.2* | × 100 | 4,420* |
| 1/500* | 8147* | 76.0* | 43.2* | × 500 | 21,600* |
| 1/1000 | 7548 | 72.5 | 40.3 | × 1000 | 40,300 |
| 1/2000 | 6182 | 59.4 | 33.0 | × 2000 | 66,000 |
| 1/2500** | 5086** | 48.8** | 27.1** | × 2500 | 68,000** |
| 1/4000 | 2845 | 27.3 | 15.2 | × 4000 | 60,800 |
| 1/5000 | 2040 | 19.6 | 10.9 | × 5000 | 54,500 |
| 1/10,000 | 797 | 7.7 | 4.3 | × 10,000 | 43,000 |

*Determined from another assay where added CPM = 10,718 and pg = 56.8
**Dilution coming nearest to 50% binding Calculations are based on the reading at the 1/2500 dilution since at this dilution approximately 50% of the $^3$H-E$_2$ is bound. Therefore, 1 ml of the antiserum has the ability to bind 68,000 pg of E$_2$ or 68,000 pg equivalent antibody (PEA) units.

It has been found that from about 15,000 to about 25,000 PEA units per pound body weight is a sufficient dosage to inhibit estrus and fertility in dogs. A preferred unit dose is 0.05 ml (0.05 ml = 20,000 PEA units) per pound body weight. The antiserum is standarized by either concentrating or diluting the antiserum to the preferred unit dosage and subsequently bottle and lyophilized.

TREATMENT OF FEMALE MAMMALS

All female dogs to be treated with the antiserum of this invention were selected with known reproductive histories consisting of either one previously recorded estrus cycle or a previously successful pregnancy or both. In addition, each dog was examined prior to treatment for signs of a developing estrous cycle by observing physical signs, such as swelling of the vulva, bleeding, etc. and by obtaining vaginal smears to determine more precisely the phase of the cycle.

The changes in the cell characteristics of the vaginal mucosa are pronounced during the proestrus period. Based on all types of physical observation this proestrus period can be divided into four parts as follows:

(a) Anestrus to early proestrus (A-Pe) — There is a dramatic shift of the leucocytes and non-cornified epithelial cell ratio and an increase in the number of erythrocytes.

(b) Early proestrus (Pe) — There is a slight swelling, moistened vulva, and some attraction of the male dog. The predominate vaginal smear cell types are erythrocytes, large non-cornified and some superficial epithelial cells and a definite increase in erythrocytes.

(c) Mid-proestrus (Pm) — The female is generally restless and attracts the male, but will not accept the male. There is a definite protrusion and swelling of the vulva, accompanied by a heavy blood discharge. The Pm phase is usually associated with the third day of persisting vulvar bleeding. The vaginal smear pattern depicts erythrocytes, large non-cornified, superficial and cornified epithelial cells.

(d) Late proestrus (Pl) — The female attracts but will not accept the male. Her disposition at this time is either cranky or very playful. Vulvar swelling and bleeding is maximal, with decreased bleeding towards the onset of actual estrus. Vaginal smear pattern is predominately erythrocytes and cornified epithelial cells.

Using 20,000 Picrogram Equivalent Antibody (PEA) units per pound body weight, a total of 47 female dogs were inoculated I.M. or I.V. The animals were divided into 3 groups: early proestrus (Group A), mid-proestrus (Group B), and late proestrus (Group C). The results are summarized in Table II.

Nineteen bitches inoculated during the Pe period (Group A) never exhibited any signs of attractiveness to the male during the expected time of proestrus and estrus. Four females, #4017, #3912, Miniature Poodle, and #4839 showed a delay of estrus of 25, 32, 37, and 64 days, respectively. Temporary sterilization as defined by this invention is noted in terms of either a delay of or a bypass of the expected estrus. Delay of estrus is defined as a return of the bitch to estrus following treatment without exhibiting a full estrous cycle. In contrast, bypass means that the treated animal returns to estrus following a complete estrous cycle. One dog (D16) died 44 days post the expected time of estrus from a dog fight. The remaining 14 of 19 dogs (74%) completely bypassed the estrus period and went into an anestrus phase. The duration from the bypassed estrus period (treatment estrus) to the next estrus period ranged from 122 to 346+ days for these 14 dogs.

None of the 10 dogs in Group B developed an estrus (heat) period or showed any signs that attracted males within 24–48 hours post injection. One of the 10 dogs (D19) maintained slight proestrus symptoms for 21 days post-injection and subsequently went into a short anestrus period and returned to estrus 53 days following the expected estrus period. One other dog (#1673) died from a dogfight 48 days post expected estrus and exhibited full anestrus symptoms at the time of death.

TABLE II

Summary of Effects on the Estrus Cycle in Female Dogs
Receiving 20,000 PEA Units of Antibody per Lb. Body Weight

| GROUP A |
|---|

Delay From**
Expected

TABLE II-continued
Summary of Effects on the Estrus Cycle in Female Dogs Receiving 20,000 PEA Units of Antibody per Lb. Body Weight

| Breed | Dog # | Adm.* Route | Date of Adm. | Cycle State When Adm. | Expected Estrus | Estrus (days) |
|---|---|---|---|---|---|---|
| Beagle | 6599 | I.V. | 3/27/75 | Pe | 4/4/75 | B(194) |
| Beagle | 11180 | I.V. | 4/1/75 | Pe | 4/10/75 | B(328+) |
| Beagle | 11635 | I.V. | 4/1/75 | A-Pe | 4/12/75 | B(277+)*** |
| Beagle | 3997 | I.M. | 4/3/75 | A-Pe | 4/14/75 | B(324+) |
| Beagle | 4839 | I.M. | 4/3/75 | A-Pe | 4/15/75 | D(64) |
| Beagle | 3795 | I.M. | 4/8/75 | Pe | 4/16/75 | B(322+) |
| Beagle | 13550 | I.M. | 4/8/75 | A-Pe | 4/17/75 | B(260) |
| Beagle | 3912 | I.M. | 4/10/75 | Pe | 4/17/75 | D(32) |
| Beagle | 8018 | I.M. | 4/17/75 | Pe | 4/27/75 | B(215) |
| Beagle | 11534 | I.M. | 4/17.75 | Pe | 4/25/75 | B(210) |
| Border Collie | 1582 | I.V. | 3/14/75 | Pe | 3/23/75 | B(346+) |
| Mongrel | 1677 | I.V. | 3/14/75 | A-Pe | 3/24/75 | B(295) |
| Mongrel | 1636 | I.M. | 4/2/75 | A-Pe | 4/12/75 | B(167) |
| Pekingese | — | I.M. | 6/13/75 | Pe | 6/18/75 | B(259+) |
| Black Lab. | D16 | I.M. | 6/20/75 | Pe | 6/28/75 | 44+*** |
| Black Lab. | D21 | I.M. | 6/4/75 | Pe | 6/10/75 | B(122) |
| Cocker Spaniel | — | I.M. | 6/25/75 | Pe | 7/4/75 | B(243+) |
| Miniature Poodle | — | I.M. | 1/22/76 | Pe | 1/29/76 | D(37) |
| Beagle | 4017 | I.M. | 11/20/75 | Pe | 11/27/75 | D(25) |

Group B

| Breed | Dog # | Adm.* Route | Date of Adm. | Cycle State When Adm. | Expected Estrus | Delay From** Expected Extrus (days) |
|---|---|---|---|---|---|---|
| Beagle | D07 | I.M. | 5/22/75 | Pm | 5/25/75 | B(157) |
| Beagle | 10107 | I/M. | 4/30/75 | Pm | 5/5/75 | B(142) |
| Mongrel | 1673 | I.M. | 3/21/75 | Pm | 3/28/75 | 48+*** |
| Border Collie | 1713 | I.M. | 3/26/75 | Pm | 3/30/75 | B(339+) |
| Boxer | — | I.M. | 5/29/75 | Pm | 6/4/75 | B(273+) |
| Brittany | — | I.M. | 6/4/75 | Pm-Pl | 6/7/75 | B(270+) |
| Collie | 1647 | I.M. | 6/17/75 | Pm | 6/20/75 | B(203) |
| Pointer | D18 | I.M. | 6/4/75 | Pm | 6/11/75 | B(226+) |
| Pointer | D19 | I.M. | 6/20/75 | Pm | 6/28/75 | B(53) |
| Black Lab. | D24 | I.M. | 6/20/75 | Pm | 6/26/75 | B(251+) |

Group C

| Breed | Dog # | Adm.* Route | Date of Adm. | Cycle State When Adm. | Expected Estrus | Delay From** Expected Estrus (days) |
|---|---|---|---|---|---|---|
| Beagle | 8996 | I.V. | 3/21/75 | Pl | 3/23/75 | N.D. |
| Beagle | 5947 | I.V. | 3/7/75 | Pl | 3/9/75 | N.D. |
| Beagle | 1895 | I.V. | 2/26/75 | Pl | 2/28/75 | B(190)**** |
| Beagle | 1901 | I.V. | 2/26/75 | Pl | 2/28/75 | N.D. |
| Beagle | 7870 | I.M. | 4/25/75 | Pl | 4/27/75 | B(311+) |
| Beagle | 5731 | I.M. | 4/30/75 | Pl | 5/2/75 | D(86)*** |
| Beagle | Y183 | I.M. | 5/1/75 | Pl | 5/3/75 | N.D. |
| Beagle | 4824 | I.M. | 5/7/75 | Pl | 5/9/75 | N.D. |
| Mongrel | 1676 | I.V. | 4/2/75 | Pl | 4/4/75 | B(227) |
| Mongrel | 1678 | I.V. | 4/2/75 | Pl | 4/4/75 | B(211) |
| Border Collie | 1714 | I.V. | 4/2/75 | Pl | 4/4/75 | B(194) |
| Red Tick | 1559 | I.V. | 4/9/75 | Pl | 4/11/75 | N.D. |
| Mongrel | 1584 | I.V. | 4/9/75 | Pl | 4/11/75 | B(206) |
| Mongrel | 1645 | I.M. | 4/9/75 | Pl | 4/11/75 | B(161) |
| Keeshund | — | I.M. | 8/5/75 | Pl | 8/8/75 | B(149) |
| Boxer | — | I.M. | 8/25/75 | Pl | 8/27/75 | N.D. |
| Collie | — | I.M. | 12/10/75 | Pl-E | 12/11/75 | N.D. |
| Beagle | 4120 | I.M. | 4/30/75 | Pl | 5/2/75 | N.D. |

*Dosage given I.V. was via the jugular vein; I.M. administration was in 2 sites (thighs)
**N.D. - No Delay - Those dogs that came into estrus at the expected time
Values folloed by a plus (+) sign denote that these dogs have yet to return to estrus following treatment
***Died from dog fights
****Time estrus would have occurred if not retreated
D = Delay - Those dogs returning to estrus following treatment without exhibiting a full estrous cycle
B = Bypass - Those dogs returning to estrus following treatment, accompanied by a full estrous cycle In Group C, 9 of 18 dogs (50%) did not exhibit estrus when expected. Three of these 9 dogs (#1676, #1678, #1714) maintain a somewhat bloody vaginal discharge for a few days following injection. These 3 dogs began to exhibit a vaginal smear resembling the anestrus phase within 2 to 3 weeks following serum inoculation. The remaining 9 dogs came into heat on the date the estrus period was to begin.

Studies confirm that in those dogs where antiserum was effective, swelling of the vulva subsided and sanguineous vaginal discharge disappeared within 24-48 hours following treatment in approximately 90% of the bitches. However, 100% of the bitches where antiserum was effective ceased to attract the male and vaginal smears showed no cell characteristics indicative of estrus.

Studies indicate that when antiserum is administered to bitches at the proper phase of the estrous cycle, it is completely effective for temporary sterilization of the bitch; that is to say, the antiserum is a completely effective contraceptive. All of the dogs treated during the late anestrus-early proestrus to mid-proestrus phases of the estrous cycle with 20,000 PEA unit per pound of body weight exhibited complete contraception.

Serum samples were obtained from 35 of the bitches (Groups A,B,C) at varying intervals and assayed for estradiol antibody titer. The results are seen in Table III.

TABLE III

Individual Titration Data in Female Dogs Receiving 20,000 PEA Units of Antibody per Lb. Body Weight

GROUP A pg $^3$H-E$_2$ Bound per ml Serum (Days)

| Dog No. | 1 | 2 | 3 | 4 | 7 | 8 | 15 | 22 | 29 |
|---|---|---|---|---|---|---|---|---|---|
| 6599 | — | — | — | 286 | — | 283 | 84 | 62 | 64 |
| 11180 | 323 | 317 | 328 | — | — | — | — | — | — |
| 11635 | 341 | 350 | 345 | — | — | — | — | — | — |
| 3997 | 342 | — | — | 297 | 199 | 166 | 139 | 85 | 34 |
| 4839 | 345 | — | — | 318 | 218 | 207 | 168 | 107 | 45 |
| 3795 | 322 | 310 | 273 | — | — | 225 | — | — | — |
| 13550 | 272 | 268 | 246 | — | — | 224 | — | — | — |
| 3912 | 320 | — | — | 274 | — | 259 | 148 | 57 | 39 |
| 8018 | 290 | — | — | 313 | — | 270 | 123 | 75 | 66 |
| 11534 | 276 | — | — | 310 | — | 235 | 84 | 53 | 39 |
| 1582 | — | — | 310 | — | 253 | — | — | — | 31 |
| 1677 | — | — | 337 | — | 295 | — | — | — | 50 |
| 1636 | 369 | 362 | — | — | 224 | — | 189 | — | 54 |
| Pekingese | — | — | — | — | — | — | — | — | — |
| D16 | — | — | — | — | — | — | — | — | — |
| D21 | — | 359 | — | — | 361 | — | 228 | — | — |
| Cocker | — | — | — | — | — | — | — | — | — |
| 4017 | — | — | — | 193 | — | — | — | — | — |
| Miniature Poodle | — | — | — | — | — | — | — | — | — |
| Average | 320 | 328 | 307 | 284 | 258 | 234 | 145 | 73 | 47 |
| Number | 10 | 6 | 6 | 7 | 6 | 8 | 8 | 6 | 9 |
| Range | 272–369 | 268–362 | 246–345 | 193–318 | 199–361 | 166–283 | 84–228 | 53–107 | 31–66 |

GROUP B pg $^3$H-E$_2$ Bound per ml Serum (Days)

| Dog No. | 1 | 2 | 5 | 7 | 9 | 11 | 13 | 15 | 23 | 30 |
|---|---|---|---|---|---|---|---|---|---|---|
| D07 | 390 | — | 366 | 332 | — | 266 | 224 | 197 | 82 | 58 |
| 10107 | 324 | 321 | 313 | 262 | 217 | — | — | 150 | 84 | 59 |
| 1673 | — | — | 314 | — | — | — | 230 | — | — | 69 |
| 1713 | 362 | — | 312 | 284 | 267 | — | — | 126 | 93 | 68 |
| Boxer | 316 | — | 330 | 325 | — | 210 | 186 | 156 | 100 | — |
| Brittany | — | — | — | — | — | — | — | — | — | — |
| Collie | — | — | — | — | — | — | — | — | — | — |
| D18 | — | 332 | 273 | 206 | 155 | — | 175 | 54 | — | — |
| D19 | — | — | — | — | — | — | — | — | — | — |
| D24 | — | — | — | — | — | — | — | — | — | — |
| Average | 348 | 327 | 318 | 282 | 213 | 238 | 204 | 157 | 90 | 64 |
| Number | 4 | 2 | 6 | 5 | 3 | 2 | 4 | 5 | 4 | 4 |
| Range | 316–390 | 321–332 | 273–366 | 206–332 | 155–267 | 210–266 | 175–230 | 126–197 | 82–100 | 58–69 |

GROUP C pg $^3$H-E$_2$ Bound per ml Serum (Days)

| Dog No. | 1 | 2 | 5 | 7 | 9 | 12 | 14 | 16 | 23 | 30 |
|---|---|---|---|---|---|---|---|---|---|---|
| 8996 | — | — | 323 | — | — | 178 | 172 | — | — | — |
| 5947 | — | — | 388 | 368 | — | — | 252 | — | — | — |
| 1895 | 370 | 387 | 379 | 393 | 383 | 361 | 348 | 312 | 206 | — |
| 1901 | 396 | 381 | 359 | 382 | 362 | 363 | 345 | 314 | 228 | — |
| 7870 | — | — | 233 | 218 | — | 105 | 113 | — | — | — |
| 4120 | 330 | 327 | 273 | 213 | 218 | — | — | 148 | 72 | 52 |
| 5731 | 309 | 297 | 269 | 227 | 216 | — | — | 118 | 75 | 51 |
| Y183 | — | — | — | — | — | — | — | — | — | — |
| 4842 | 275 | 286 | 219 | 165 | 238 | — | — | 138 | 90 | 40 |
| 1676 | 353 | 351 | 291 | — | 211 | — | — | 143 | 91 | 41 |
| 1678 | 342 | 351 | 287 | 232 | 184 | — | — | 159 | 101 | 41 |
| 1714 | 332 | 312 | 248 | 156 | 151 | — | — | 136 | 78 | 39 |
| 1559 | 268 | 275 | 253 | 274 | 293 | — | 184 | — | 76 | 59 |
| 1584 | 303 | 293 | 258 | 307 | 299 | — | 162 | — | 70 | 45 |
| 1645 | 326 | 312 | 276 | 332 | 308 | — | 195 | — | 94 | 52 |
| Keeshound | — | — | — | — | — | — | — | — | — | — |
| Boxer | — | — | — | — | — | — | — | — | — | — |
| Collie | — | — | — | — | — | — | — | — | — | — |
| Average | 328 | 325 | 290 | 272 | 260 | 252 | 221 | 184 | 107 | 47 |
| Number | 11 | 11 | 14 | 12 | 11 | 4 | 8 | 8 | 11 | 9 |
| Range | 268–396 | 275–387 | 219–388 | 156–393 | 151–383 | 105–363 | 113–348 | 118–314 | 70–228 | 39–59 |

Regardless of the phase of proestrus, the antibody levels appear to reach the same levels and persist about the same length of time. Since the bitch produces at maximum approximately 70 pg estradiol-17 beta (E$_2$) per ml serum (Nett, T. M., A. N. Akbar, R. D. Phemister, P. A. Hoist, L. E. Reichert, Jr., and G. D. Niswender, 1975. Levels of luteinizing hormone, estradiol and progesterone in serum during the estrous cycle and pregnancy in the Beagle bitch. Proc. Soc. Exp. Biol. Med. 148:134), one needs to administer enough antisera to neutralize this 70 pg/ml. It is well documented that approximately 7% of the bitch's body weight is blood and that approximately 50% of the blood is serum. Therefore, for every pound of body weight there is approximately 16 ml serum containing 1120 pg of E$_2$. It would appear that enough antibody present to neutralize 1120 pg of E$_2$ would be sufficient. However, this has not been the case. It takes about 15,000 to about 25,000 PEA units to prevent estrus and fertility in the bitch. An effective antibody level can be maintained for neutralization of 70 pg of E$_2$ per ml serum for approximately 20 days following a single inoculation as seen in Table III.

Studies indicate that bitches which have returned to normal estrus following treatment with the antiserum of this invention show no impairment of fertility. Seven receiving the antiserum to estradiol-17 beta were bred.

Six of the 7 dogs received 20,000 PEA units per pound of body weight at various stages of proestrus. One dog received 40,000 PEA units per pound of body weight during late proestrus. Of the seven bitches bred, all seven conceived and whelped an average of 5.2 pups per litter. It is interesting to note that the bitch receiving twice the amount (40,000 PEA units) whelped 8 pups. The above results indicate that the treatment does not impair the normal reproductive process.

An investigation was made to determine a minimal effective dosage level for the temporary sterilization of bitches. In this investigation, PEA unit levels per pound of body weight of 10,000 (Group 1, 19 dogs), 6800 (Group 2, 5 dogs), 5000 (Group 3, 10 dogs) and 3400 (Group 4, 7 dogs) were utilized. The results of this particular study revealed that seven of nineteen (7/19), 1/5, 2/10, and 1/7 bitches exhibited no delay of estrus for groups 1, 2, 3, and 4, respectively. Further test results indicated that 4/19, 1/5, 1/10, and 5/7 exhibited a delay and 8/19, 3/5, 7/10, and 1/7 dogs exhibited a bypass for groups 1, 2, 3, and 4, respectively. One distinct observation noted for those dogs displaying a bypass was a full estrus vaginal smear accompanied by vulvar swelling and a light sanguineous discharge after a few days following treatment, although no male acceptance was noted. This condition was observed in 5/8, 2/3, 7/7, and 1/1 dogs of groups 1, 2, 3, and 4, respectively.

This data indicates that the level of 10,000 PEA units and below per pound body weight does not give satisfactory contraception as measured by delay or bypass of estrus. Thus a level of from about 15,000 to about 80,000 PEA units per pound of body weight is preferred for satisfactory contraception. That is to say, the antiserum levels required for satisfactory temporary sterilization of the female canine should be at minimum 15,000 PEA units per pound of dog body weight. It is to be understood, of course, that the upper limit of antiserum administered is dilineated only by extraneous considerations.

In summary, this invention is directed to the discovery that antisera against an estrogen, which is essential to the reproductive cycle of a female mammal, can be prepared by the immunological system of a donor mammal, separated from the blood of the donor, and used to temporarily sterilize the female. This has been graphically illustrated by the use of female dogs as exemplary of the mammals. The concept of the invention may, of course, be applied to other mammalian species, such as humans, cows, horses, pigs, and the like. Although the concept is directed at blocking the reproductive cycle of the female of the species, it is also contemplated that an antiserum against a necessary hormone to the reproductive process of the male may also be prepared following the teaching of this invention.

In the selected species used herein for purposes of illustration of the inventive concept, the canine species, the antiserum to the $E_2$ was prepared. The estrogen was reacted with succinic anydride to form the hemisuccinate and this derivative was coupled to Keyhole Limpet Hemocyanin (KLH) to form a steroid protein conjugate against which the immunological system of a donor would form antibodies to $E_2$.

It was found that best results could be obtained if 1600 to 2200 molecules of the $E_2$ were coupled to each molecule of KLH. It is to be recognized, of course, that a much wider range than this is operable and it is contemplated that a carrier having attached thereto from about 500 to about 5000 molecules of $E_2$ would cause the formation of a sufficient level of antibodies (titer) in the donor animal to be operable.

It was also found that optimum results with respect to antibody titer in the donor animal were obtained if the animal was given an initial parenteral injection of the antigen, along with the usual adjuvant, followed by booster injections at periodic intervals.

One important factor in obtaining satisfactory results with the antiserum of this invention was found to be the antibody level, or concentration, administered to the female. As a result of careful experimentation, it was determined that optimum results were obtained when from about 15,000 to about 25,000 PEA units per pound of body weight of the female dog to be treated were administered. It is to be understood, of course, that for different species, different levels of estrogen antibodies may be required. Functionally speaking, sufficient antibodies to effectively neutralize the estrogen levels required for a normal reproductive cycle must be administered.

Another important aspect of the inventive concept, as applied to the canine species, is the timing in the estrous cycle for the administration of the antiserum. Optimal results have been obtained by administering the antiserum to the female dog during the late anestrus-early proestrus to mid-proestrus phase of the estrous cycle.

To summarize briefly, the present invention relates to a injectable contraceptive antiserum, a method of preparing said antiserum and the method of preventing conception in mammals by the use of said antiserum, is disclosed. An antigen which causes the production of antibodies directed against a hormone essential to the reproductive cycle of mammal is prepared by coupling such a hormone with a carrier to form a hormone-carrier conjugate, a mammal in injected with said conjugate, and the produced antiserum is recovered from blood from said mammal. Conception in mammals is prevented by injection of such recovered antiserum during the proper period of the reproductive cycle of said mammal.

As will be readily apparent to those skilled in the art, upon reading the above detailed description and examples, various modifications can be made thereto without departing from the spirit of the present invention and such scope of said invention shall be limited only by the scope of the appended claims.

What is claimed is:

1. A method of causing a delay or bypass of estrus in a female canine having a known reproductive history consisting of either at least one previous estrus cycle, a previously successful pregnancy or both which comprises parenterally administering to said canine, during late anestrus to mid-proestrus, at least 15,000 picogram equivalent antibody units per pound of body weight of a contraceptive antiserum that has been prepared by a process of:

(a) preparing an antigen which is capable of stimulating the immunological system of a female canine to form antibodies against estradiol-17 beta by the esterification of the hydroxyl groups of estradiol-17 beta with succinic anhydride to form the estradiol-17 beta hemisuccinate and coupling said hemisuccinate to the amino groups of a protein selected from the group consisting of keyhole limpet hemocyanin, bovine serum albumin and human serum albumin in an amount such that to each molecule of protein there is attached 500–5000 molecules of the estradiol-17 beta.

(b) initially parenterally administering to a female canine donor at intramuscular sites and multi-intradermal sites 1 mg of said antigen emulsified in 2 ml of an adjuvant therefor, parenterally administering additional doses of said emulsified antigen at periodic intervals to cause the production of a desired level of antibodies to said antigen by the immunological system of said donor;

(c) collecting blood from said female canine donor in a manner to prevent coagulation of said collected blood, recovering the plasma of said blood by centrifugation, defibrinating said plasma to obtain antiserum containing said antibodies; and (d) diluting said antiserum in a buffered solution of a preservative therefor to a desired concentration.

2. The method of claim 1 wherein the protein is keyhole limpet hemocyanin.

3. The method of claim 2 wherein after centrifugation the plasma is shaken with calcium chloride to form fibrin and the fibrin is removed by filtration.

4. The method of claim 1 wherein the antiserum is diluted to a concentration of 1:10,000.

5. The method of claim 1 wherein about 15,000–25,000 picogram equivalent antibody units is administered per pound of body weight.

6. The method of claim 2 wherein to each molecule of the keyhole limpet hemocyanin there is attached 1600–2200 molecules of the hemisuccinate.

7. The method of claim 1 wherein the hemisuccinate is coupled to the protein via the carbodiimide reaction.

8. The method of causing a delay or bypass of estrus in a female canine which comprises parenterally administering to a female canine with a known reproductive history consisting of either one previous estrous cycle, a previously successful pregnancy or both, an effective amount in the order of 15–80,000 picogram equivalent antibody units per pound of body weight during late anestrus to mid-proestrus of the reproductive cycle of a contraceptive antiserum which has been prepared by a process which comprises the steps of:

(a) preparing an antigen which is capable of stimulating the immunological system of a female canine to form antibodies against estradiol-17 beta by the esterification of the hydroxyl groups of estradiol-17 beta with succinic anhydride to form the estradiol-17 beta-hemisuccinate and coupling said hemisuccinate to the amino groups of keyhole limpet hemocyanin via the carbodiimide reaction in amounts such that to each hemocyanin molecule 1600–2200 of the hemisuccinate molecules are attached;

(b) initially injecting parenterally a female canine donor with 1 mg of antigen, emulsified in 2 ml. of an adjuvant, into multi-intradermal sites and intramuscular sites, followed by secondary injections of said emulsified antigen at periodic intervals for periods of time such that the immunological system of said female canine donor can produce antibodies to said antigen at the desired level;

(c) collecting blood from said female canine donor in a vessel containing an anticoagulant, recovering the plasma of said blood by centrifugation;

(d) converting said plasma to an injectable antiserum by shaking with calcium chloride to form fibrin, removing fibrin by filtration, diluting said antiserum with a buffered preservative solution to a concentration of 1:10,000 and sterile filtering said antiserum.

* * * * *